United States Patent [19]

Ruest

[11] Patent Number: 4,777,289

[45] Date of Patent: Oct. 11, 1988

[54] PROCESS FOR THE PREPARATION OF ALKYLTHIOALKANOATE SALTS

[75] Inventor: Dennis A. Ruest, Manchester, Mo.

[73] Assignee: Monsanto Company, St. Louis, Mo.

[21] Appl. No.: 860,949

[22] Filed: May 8, 1986

[51] Int. Cl.$^4$ ............................................ C07C 147/02
[52] U.S. Cl. ................................... 562/581; 562/556; 562/557; 562/559; 562/606; 562/426; 562/427; 562/428; 568/69; 568/716
[58] Field of Search ............... 562/581, 556, 559, 557, 562/606, 426, 427, 428; 568/69, 716

[56] References Cited

U.S. PATENT DOCUMENTS

| | | | |
|---|---|---|---|
| 2,168,851 | 8/1939 | Yabroff et al. | 568/69 |
| 2,236,723 | 4/1941 | Yabroff et al. | 568/69 |
| 2,556,414 | 6/1951 | Brooks et al. | 568/69 |
| 2,560,178 | 7/1951 | Krause et al. | 568/69 |
| 2,727,065 | 12/1955 | Anagnostopoulos | 562/581 |
| 2,745,745 | 5/1956 | Blake et al. | 562/581 |
| 2,946,818 | 7/1969 | Anagnostopoulos | 562/581 |
| 3,663,624 | 5/1972 | Jones | 568/69 |
| 3,671,212 | 6/1972 | Jaworski | 71/77 |
| 4,045,587 | 8/1977 | Katz et al. | 426/533 |
| 4,059,579 | 11/1977 | Ruest et al. | 544/172 |
| 4,080,376 | 3/1978 | Shen et al. | 260/534 E |
| 4,126,627 | 11/1978 | Reifenberg | 568/69 |
| 4,177,198 | 12/1979 | Bohen | 568/69 |
| 4,319,047 | 3/1982 | Komorn et al. | 568/41 |

FOREIGN PATENT DOCUMENTS

| | | |
|---|---|---|
| 2271207 | 12/1975 | France . |
| 816544 | 10/1951 | German Democratic Rep. . |
| 1071 | 2/1955 | Japan . |
| 651165 | 3/1951 | United Kingdom ................ 562/581 |

OTHER PUBLICATIONS

Pleininger, "The Cleavage of Gamma-Butyrolactone and Alpha-Amino-Gamma-Butyrolactone with Sodium Methyl Mercaptide or Selenide. A Synthesis of Methionine." 83 Chem. Ber., 265–268 (1950), (English translation).

Chemical Abstracts 51:2853c (1957), re Japan 1071 (1955).

Chemical Abstracts 47:2200e, re German Pat. No. 816,544 (10/11/51).

Derwent Publications Ltd., Abstract 17334X/10 of French Pat. No. 2,271,202 (5/16/74).

Derwent Publications Ltd., Abstract 85-057331/10 of European Pat. Appln. No. 1,337,796A (3/6/85).

Primary Examiner—Paul F. Shaver
Assistant Examiner—Bruce D. Gray
Attorney, Agent, or Firm—Jon H. Beusen; George R. Beck

[57] ABSTRACT

A process for the preparation of alkylthioalkanoate salts by reaction of an alkali metal alkylmercaptide with a lactone in the presence of an aprotic polar organic solvent. Preferably, the alkali metal mercaptide is prepared by reaction of an alkylmercaptan and an alkali metal phenate.

26 Claims, No Drawings

PROCESS FOR THE PREPARATION OF ALKYLTHIOALKANOATE SALTS

BACKGROUND OF THE INVENTION

This invention relates to the synthesis of alkali metal salts of methionine and its analogs and, more particularly, to an improved process for the synthesis of such compounds in high yields without the necessity of using acrolein or hydrogen cyanide as precursors.

The hydroxy analog of methionine, i.e., 2-hydroxy-4-methylthiobutyric acid, is widely used as an animal feed supplement. According to a conventional process for the preparation of 2-hydroxy-4-methylthiobutyric acid (HMBA), 2-hydroxy-4-methylthiobutyronitrile (HMBN) is hydrolyzed with a mineral acid. As described for example in Blake et al. U.S. Pat. No. 2,745,745, HMBN is typically prepared by reacting 3-methylthiopropionaldehyde with hydrogen cyanide. The 3-methylthiopropionaldehydyde intermediate is in turn prepared by condensation of acrolein and methyl mercaptan. Thus, in the commercial manufacture of HMBA, acrolein and hydrogen cyanide have been essential starting materials.

The toxicity of hydrogen cyanide is well known. Acrolein is also toxic, and both materials are flammable as well. Accordingly, the shipping and handling of these raw materials is costly.

Accordingly, there has been a long standing need for commercially feasible processes for the manufacture of 2-hydroxy-4-methylthiobutyric acid and related compounds without the necessity of using acrolein and hydrogen cyanide as precursor materials.

Plieninger, "Cleavage of gamma-Butyrolactone and alpha-Amino-butyrolactone with Sodium Methylmercaptide or Selenide. A Synthesis of Methionine.", Chem. Ber., vol. 83, pages 265–268 (1950), Chem. Abstracts, 44:9919b describes the reaction of unsubstituted butyrolactone and sodium methylmercaptide in a toluene medium. The reference also describes the formation of methionine by reaction of sodium methylmercaptide with alpha-amino-butyrolactone in toluene. Further described in the reference is a reaction of alpha-amino-butyrolactone with sodium methyl selenide. Neutralization with acetic acid converts the alkali metal salt products of these reactions to the corresponding free acids. Plieninger further describes the preparation of sodium methylmercaptide by passing methyl mercaptan into methanol containing metallic sodium, concentrating the resultant mixture by evaporation of solvent, adding toluene, and distilling off solvent until the boiling point of toluene is reached. Alternatively, metallic sodium is added to a solution of methyl mercaptan and liquid ammonia, following which toluene is added and ammonia evaporated to precipitate an amorphous sodium methylmercaptide.

British Pat. No. 651,165 also describes the preparation of methionine by the reaction of alpha-amino-butyrolactone with sodium methyl mercaptide. The examples in this patent describe both a violent reaction obtained by addition of alpha-amino-butyrolactone (neat) to dry sodium methylmercaptide (neat), and a suspension reaction in xylene. Reaction is carried out at a temperature of 150°–200° C. The sodium salt of methionine obtained from the reaction is acidified with acetic acid to pH 7. As prior art, the British patent also describes the preparation of methionine by benzoylation of alpha-aminobutyrolactone, conversion of the N-benzoyl compound to a gamma-chloro-alpha-benzoylaminobutyric acid ester by treatment with alcoholic hydrochloric acid, and reaction of the ester with sodium methylmercaptide to produce N-benzoyl methionine. The benzoyl blocking group is removed by hydrolysis to produce methionine.

German Pat. No. 816,544 (Chem. Abstracts, vol. 47: 2200e) describes a process for preparing gamma-alkylthio or -seleno fatty acids or their amino derivatives by reaction of the corresponding alkali metal alkylmercaptide or -selenide with gamma-lactones at temperatures in the range of 100°–200° C. in the presence of an inert solvent such as benzene or toluene. The examples of this patent illustrate reaction of sodium methylmercaptide with gamma-butyrolactone in a toluene suspension. Further examples show use of the same toluene medium for the preparation of methionine from sodium methylmercaptide and alpha-amino-gamma-butyrolactone.

Chem. Abstracts 51:2853c describes still another process in which a toluene medium is used for reaction of sodium methylmercaptide with a gamma-butyrolactone. In this case the lactone substrate is alpha-benzoylamino-gamma-butyrolactone and the benzoyl protecting group is removed by neutralization with sodium carbonate to produce D,L-methionine. While the methods described in Pleininger, British Pat. No. 651,165, German Pat. No. 816,544, and CA 51:2835c have been shown to be effective for the preparation for alkylthiobutyric acid salts, the yields obtainable by reaction in inert solvents such as toluene and xylene have not been commercially attractive.

Aries French Pat. No. 2,271,207, describes a process for the preparation of methionine in which 3-methylthiopropylisonitrile is reacted with a dialkyl carbonate in the presence of sodium hydride, and the product of this reaction is hydrolyzed to methionine. Reaction between the 3-methylthiopropylisonitrile and dialkyl carbonate is carried out in dimethylformamide, after which that solvent is removed by evaporation and the residue washed with pentane and dissolved in methanol. Hydrolysis is carried out by addition of hydrochloric acid, and methionine is recovered by evaporating the methanol and HCl, washing the residue with isopropyl ether, adding sodium hydroxide to pH 6, and crystallizing the product from methanol. The 3-methylthiopropylisonitrile starting material is said to be prepared readily from methylthiopropylamine in accordance with the description in Tetrahedron Letters, 1972, p. 1637.

Jaworski U.S. Pat. No. 3,671,212 describes the preparation of a salt of 2-hydroxy-4-methylthiobutyric acid by hydrolysis of HMBN. HMBN is prepared by condensation of methyl mercaptan with 2-hydroxy-4-chlorobutyronitrile. The reference does not disclose the method of preparation of the 2-hydroxy-4-chlorobutyronitrile.

SUMMARY OF THE INVENTION

It is the object of the invention to provide a novel process for the preparation of alkali metal salts of methionine, HMBA, and other related compounds; to provide such a process which avoids the need for use of acrolein as a precursor compound; to provide such a process which avoids the need for using hydrogen cyanide as a precursor compound; to provide such a process which provides the product alkali metal salt in high yield; and to provide a process which affords economically acceptable productivity in the manufacture of the aforesaid products.

Briefly, therefore, the present invention is directed to a process for the preparation of a compound corresponding to the formula:

wherein $R^1$ is lower alkyl, M is alkali metal, n is an integer between 2 and 4, inclusive, and $R^2$ is hydrogen, hydroxyl, amino,

 or

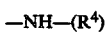

where $R^3$ is selected from among alkyl and aryl, and $R^4$ is selected from among alkyl, aryl, acyl. In accordance with the process, an alkali metal mercaptide corresponding to the formula;

where $R^1$ and M are as defined above is reacted in the presence of an aprotic polar organic solvent with a lactone corresponding to the formula:

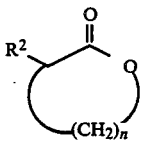

where $R^2$ and n are as defined above.

The invention is further directed to a process for the preparation of a compound corresponding to the formula:

where $R^1$, M, n, and $R^2$ are as defined above. In accordance with the process, a lower alkyl mercaptan corresponding to the formula:

where $R^1$ is as defined above, is reacted with an alkali metal phenate to produce an alkali metal mercaptide corresponding to the formula:

where $R^1$ and M are as defined above. The alkali metal mercaptide is reacted in the presence of an aprotic polar organic solvent with a lactone corresponding to the formula:

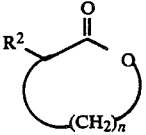

where $R^2$ and n are as defined above.

The invention is further directed to a process for the preparation of an alkylthioalkanoate compound of the aforesaid type. In the process, a lower alkyl mercaptan of the type defined above, a lactone of the type defined above, and an alkali metal phenate are admixed and reacted in the presence of an aprotic polar organic solvent. The resulting mixture is maintained at a temperature of at least 80° C. for time sufficient to form the alkylthioalkanoate compound.

Further included in the invention is a process for the preparation of an alkylthioalkanoate compound of the aforesaid type, in which process a charge mixture is prepared by mixing a source of an alkylmercaptide group and a lactone in an alkaline medium comprising an aprotic polar organic solvent. The mercaptide group corresponds with the formula:

where $R^1$ is as defined above, and the lactone corresponds to the formula set forth above. The mixture so prepared is maintained at a temperature of at least 80° C. for a time sufficient to form the thioacid compound.

The invention is further directed to a process for preparing an alkylthioalkanoate compound of the aforesaid type in which a substituted or unsubstituted phenol is initially reacted with an alkali metal hydroxide in a crude base reaction system comprising a solvent selected from among pyridine and aprotic ring substituted pyridines which form low boiling azeotropes with water. The water is removed from the crude base reaction system by azeotropic distillation, thereby forming a substantially anhydrous base reagent mixture; and an alkylmercaptan is reacted with the alkali metal phenate, thereby producing an alkali metal mercaptide corresponding to the formula:

$$R^1-S-M$$

where $R^1$ and M are as defined above. The alkali metal mercaptide is reacted, in the presence of an aprotic polar organic solvent, with a lactone corresponding to the formula set forth above.

Further contemplated by the invention is a process for producing an alkylthioalkanoate compound of the aforesaid type. In the process, a substituted or unsubstituted phenol is reacted with an alkali metal hydroxide in a crude base reaction system comprising a solvent selected from the group consisting of pyridine and aprotic ring substituted pyridines that form low boiling azeotropes with water. Water is removed from the crude base reaction system by azeotropic distillation, thereby forming a substantially anhydrous base reagent mixture. The anhydrous base reagent mixture is admixed with methyl mercaptan and a lactone corresponding to the formula set forth above, thereby producing a final reaction mixture. The final reaction mixture is maintained at a temperature of at least 80° C. for a time sufficient to form said alkylthioalkanoate compound.

Other objects and features will be in part apparent and in part pointed out hereinafter.

DESCRIPTION OF THE PREFERRED EMBODIMENTS

In accordance with the present invention, it has been discovered that an alkali metal salt of 2-hydroxy-4-methylthiobutyric acid can be produced, in high yield and economically acceptable productivity, by reaction of alpha-hydroxybutyrolactone and an alkali metal thiomethylate in the presence of an aprotic polar organic solvent. Although the process of the invention is especially advantageous for the preparation of the alkali metal salts of HMBA, it is also effective for the synthesis of methionine salts, or the salts of unsubstituted 4-methylthiobutyric acid. More generally the process is effective for the preparation of compounds corresponding to the formula $$R^1-S-(CH_2)_n-CH(R^2)-C(O)-OM$$

where $R^1$ is a lower alkyl group, preferably containing from one to about 8 carbon atoms, $R^2$ is hydrogen, hydroxyl, amino, $$-OR^3, \text{ or}$$

$$NH-R^4$$

where $R^3$ is alkyl or aryl, $R^4$ is alkyl, aryl, or acyl, and n is an integer between 2 and 4, inclusive. Thus, generally, the alkali metal mercaptide reactant corresponds to the formula:

$$R^1-S-M$$

where $R^1$ is lower alkyl. The lactone reactant used in the process corresponds the formula

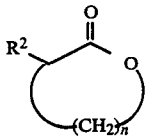

where $R^2$ is hydrogen, hydroxyl, or amino and n is an integer between 2 and 4, inclusive. Instead of the free amino group, $R^2$ may also be an ether, amide, or substituted amine, i.e. a substituent corresponding to the formula:

$$-OR^3 \text{ or}$$

$$-NH-R^4$$

where $R^3$ is alkyl or aryl and $R^4$ may be alkyl, aryl, or acyl. Where $R^3$ is alkyl it preferably contains between 1 and about 12 carbon atoms; and where it is aryl it is preferable unsubstituted phenyl or substituted phenyl having one to three substituents, each of the substituents being independently selected from among alkyl and alkoxy groups having between one and about four carbon atoms. Typical groups which may constitute $R^3$ include methyl, ethyl, propyl, octyl, dodecyl, phenyl, tolyl, and ethoxyphenyl. $R^4$ may be any of the groups which may constitute $R^3$, but may also be an acyl group. Where $R^4$ is acyl, it preferably comprises a carbonyl group substituted with any of: hydrogen; an alkyl group containing between 1 and about 12 carbon atoms; unsubstituted phenyl; or substituted phenyl having one to three substituents, each substituent of the phenyl group being independently selected from among alkyl and alkoxy having between one and about four carbon atoms. Typical acyl groups which may constitute $R^4$ include formyl, acetyl, octanoyl, benzoyl, and the like. Generally, it is not necessary to incorporate a blocking group to inhibit side reactions of an amino or hydroxyl substituent. However, the process of the invention is effective for conducting the desired synthesis with any of a variety of substituents of the aforesaid type.

It has been found that the yields attainable through the process of the invention are significantly superior to those which have been reported for the synthesis of methionine or related compounds by reaction of a sodium methyl mercaptide with either an unprotected alpha-amino-butyrolactone, a protected alpha-amino butyrolactone, or an unsubstituted butyrolactone. Although the instant disclosure is not limited to any particular theory of invention, it is believed that use of an aprotic polar organic solvent is effective for limiting side reactions and promoting attack of the lactone ring by the mercaptide. In the context of this invention, an aprotic solvent is one which does not donate protons. In particular, it is believed that the aprotic solvents used in the process are effective for solvating the alkali metal cation, but leave the mercaptide anion in a substantially non-solvated reactive condition, thereby promoting the preferred reaction and producing the 4-methylthiobutyric or other terminal alkylthioalkanoic acid salt in high yield.

The solvent which is used as the medium for reaction of the mercaptide and lactone should have a relatively high dipole moment, preferably 1 or greater, and also preferably has a dielectric constant of greater than 10. Advantageously, the reaction medium is constituted entirely of a solvent, or solvents, of such character, but the process can also be carried out in solvent mixtures containing at least 30% by weight of a solvent of the preferred type, the remainder being typically an inert solvent such as, for example, toluene or xylene. Among the particular aprotic polar solvents which are useful as media for the mercaptide/lactone reaction are dimethylformamide, hexamethyl phosphoric triamide, dimethyl sulfoxide, and tetramethylurea. However, the most preferred solvents are pyridine and ring substituted alkyl pyridines such as a picoline. Typically, a substituted pyridine solvent may have one to three alkyl substituents, each containing from 1 to about 5 carbon atoms.

In carrying out the process of the invention, a solution of the alkali metal mercaptide in the solvent is preferably prepared initially, and the lactone thereafter added to the solution. Reaction is typically conducted at a temperature in the range of 80°–150° C., most preferably 120°–130° C., under autogenous pressure. In order to minimize formation of by-products, it is important that the reaction be carried out under substantially anhydrous conditions. The presence of water or other source of protons tends to promote hydrolytic cleavage of the lactone between the carbonyl and oxygen of the ring, yielding a terminal hydroxyl group. When conducted under the preferred conditions, the reaction is typically complete within several hours, as conveniently determined by periodic sampling of the reaction mixture. Control of the end point is not generally critical for purposes other than productivity, since overreaction problems are generally not encountered.

Generally, the lactone and alkali metal mercaptide are charged to the reaction in substantially equimolar proportions. In order to maximize the reaction payload, the reactants are preferably charged to the polar solvent medium in amounts such that, during the early stages of the reaction, the alkali metal mercaptide concentration approaches or moderately exceeds the saturation point. At such concentrations, portions of both the alkali metal mercaptide reactant and the alkylthioalkanoate product may be at least partially in the solid phase. To assure even distribution of reactants and promote the progress of the reaction, the charge mixture is preferably agitated vigorously during the course of the reaction.

After completion of the reaction, the product may be recovered in any convenient fashion. For example, the reaction mixture may be diluted with water, thereby taking up the desired product in the aqueous phase. Impurities, reaction solvent, and unreacted material may then be extracted from the aqueous phase with an organic solvent, typically a halogenated solvent such as chloroform. Concentration of the raffinate under vacuum yields a residue comprising the alkali metal salt of the substituted or unsubstituted alkylthioalkanoic acid. Further purification may be achieved, for example, via recrystallization.

In an alternative process, the product is taken up in water, impurities are extracted from the aqueous phase using an organic solvent, and the aqueous phase acidified with a mineral acid to produce the free alkylthioalkanoic acid. The free acid is extracted with a polar organic solvent such as methyl isobutyl ketone, and the solvent removed by steam distillation to yield an aqueous residue containing the free acid.

The alkali metal mercaptide reactant may be prepared in any of a variety of ways. For example, it can be prepared by reaction of an alkyl mercaptan, such as methyl mercaptan, and either metallic sodium or sodium hydride. Other alkali metals and their hydrides, such as potassium metal or potassium hydride may also be used, but sodium is more economical. Preparation from sodium metal may be carried out in the manner described, for example, in Plieninger, supra. However, both metallic alkali metals and alkali metal hydrides are expensive, dangerous, and difficult to handle. Their reactions with methylmercaptan are highly exothermic and uncontrolled, making industrial scale usage normally undesirable.

In a preferred and particularly advantageous embodiment of the invention, it has been discovered that the alkali metal mercaptide may be effectively prepared by reaction between an alkyl mercaptan and an alkali metal phenate. This process substantially enhances the commercial attractiveness of the process because it avoids the need for using metallic alkali metal or alkali metal hydride. Instead, this embodiment of the invention allows the use alkali metal hydroxides, which are not only inexpensive but are also routinely used and transported in high volume commercially, as the ultimate source of the alkalinity necessary for carrying out the synthesis of alkylthioalkanoates.

In accordance with this embodiment of the invention, formation of the phenate is carried out in a crude base reaction system that is prepared by mixing a substituted or unsubstituted phenol, an alkali metal hydroxide, and a pyridine or substituted pyridine solvent. Conveniently, generally equimolar proportions of alkali metal hydroxide and phenol are charged to a reaction vessel. The reaction mixture is heated, normally under atmospheric pressure, to the boiling point of the azeotrope so that the water of reaction (as well as any other moisture contained in the charge mixture) is driven out during or subsequent to the reaction. If pyridine and unsubstituted phenol are used, therefore, the reaction mixture is typically distilled at a temperature in the range of 110°-120° C. Use of a substituted pyridine solvent increases the temperature at which the azeotrope distills off at a given pressure. By removal of water, the mixture is converted to an anhydrous base reagent containing the alkali metal phenate.

In order to minimize the formation of phenoxy substituted alkylthioalkanoate in the subsequent mercaptide/lactone reaction, it may be advantageous to use a substituted phenol in the preparation of the base reagent. Preferably, the substituted phenol used has a lower alkyl or lower alkoxy group (containing, for example, 1 to 10 carbon atoms) in a position ortho to the phenol hydroxy group. However, other substituents may be used if they are substantially inert under the conditions of the various reactions of the process of the invention; and substitutents may be located in the meta or para positions as well. Particularly suitable phenol reactants include 2-methylphenol (o-cresol), 2-ethylphenol, 2-methoxyphenol, 2,4-dimethylphenol, 2,6-dimethylphenol, and 2,4,6-trimethyl-phenol.

An alkali metal mercaptide is produced by reacting an alkyl mercaptan with the alkali metal phenate. Preferably, this reaction is effected in a system prepared by admixing the alkyl mercaptan with the anhydrous base reagent. Preferably, at least a slight excess of mercaptan, from about 1 to about 3 moles per mole of phenate is supplied to the system in which the alkali metal mercaptide is produced. This tends to exhaust the phenate and prevent its reacting with the lactone in the subsequent process steps.

The resultant mercaptide is then reacted with the lactone at 80°-150° C. in the presence of an aprotic solvent, preferably in the pyridine or substituted pyridine medium in which the phenate and mercaptide are initially prepared. In a particularly convenient method for carrying out the process, the lactone and mercaptan are charged to the reaction vessel, the reaction vessel is then sealed, and the charge mixture brought to reaction temperature for a time sufficient to complete the reaction. Preferably, the lactone charge is roughly stoichiometrically equivalent to the phenate, and the mercaptan is charged in excess, typically about 1 to about 3 moles, preferably about 2 moles, per mole of lactone. To maximize payload, the amounts charged are preferably such that the alkali metal phenate concentration is approximately at saturation. Reaction is thereafter carried out under autogenous pressure.

After the reaction is complete, as determined, for example, by periodic sampling, excess mercaptan may be removed by stripping, and the 4-methylthioalkanoate product recovered by any convenient method, for example, the method discussed hereinabove.

The following examples illustrate the invention:

EXAMPLE 1

Sodium hydroxide (4 g; 0.1 mole), phenol (9.4 g; 0.1 mole) and pyridine (75 ml) were placed in a 100 ml three neck round bottom flask, and reaction effected to produce sodium phenate. The reaction product was heated to boiling under atmospheric pressure, and water removed by azeotropic distillation. Overheads boiling out of the flask were passed through a 6 inch Vigreaux column under nitrogen. During the course of the distillation, the pot temperature ranged from 112°-118° C. and the overheads ranged from a temperature of 97°-114° C. Approximately 25 ml of water/pyridine overheads was collected.

Thereafter methylmercaptan (5 g) was introduced into the reaction flask by distilling it from a source condensing it in a dry ice condenser and allowing the condensate to flow by gravity into the sodium phenate solution in the flask. Heat was applied to the resulting mixture. After heat had been applied for 5 minutes and the temperature of the contents of the flask had risen to 75° C., addition of alpha-hydroxybutyrolactone to the contents of the flask was commenced. Addition of alpha-hydroxybutyrolactone (10 g; 0.1 mole) was carried out over a period of about 10 minutes during which time heating was continued and the temperature of the contents of the flask increased to 90° C. After addition of the alpha-hydroxybutyrolactone was completed, heating was continued for a period of 2 hours during which the temperature reached a maximum of 112° C. After heat was removed the reaction mixture was allowed to stand overnight. The next day the reaction mixture was diluted with water (25 ml) and heat reapplied for a period of about 45 minutes during which the temperature reach 97° C. After cooling, the mixture was diluted with chloroform (50 ml) and the aqueous and organic phases allowed to separate. The aqueous phase was then washed with two aliquots of chloroform (25 ml each) and stripped on a rotary evaporator. The residue was stored in a vacuum oven at approximately 110° C.

This syrup was dissolved in water (about 30 ml), acidified with concentrated sulfuric acid (5.3 g), and extracted with four aliquots of methyl isobutyl ketone (25 ml each). Thereafter the MIBK solution was stripped on a rotary evaporator and the residue twice diluted with water (25 ml each) and stripped to remove residual MIBK. The resulting product (11.3 g) was silylated and subjected to GLC analysis. GLC analysis using an n-dodecane internal standard indicated that the product was 78.6% HMBA (59% yield).

EXAMPLE 2

2,6-dimethylphenol (12.2 g; 0.1 mole), sodium hydroxide (4 g; 0.1 mole) and gamma-picoline (approximately 75 ml) were placed in a 100 ml flask. The resultant crude base reaction system was heated to its atmospheric boiling point to remove water. Overheads were distilled out of the reaction mixture through a 6 inch Vigreaux column, resulting in the collection of about 25 ml of distillate. Temperature of the overheads ranged from 95°–145° C. during the course of the distillation.

After formation of the dimethylphenate and removal of water as described above, the anhydrous base reagent mixture obtained, comprising sodium 2,6-dimethylphenate and gamma-picoline, was placed in a Fischer-Porter bottle. Methylmercaptan (10 g) and alpha-hydroxybutyrolactone (10.2 g) were then added, and the bottle sealed and placed on a oil bath. The mixture contained in the bottle was heated under autogenous pressure for a period of about 7½ hours, the temperature rising to 135° C. after ½ hour, stabilizing at 130° C. one hour later, and holding at 130°–131° C. throughout the remainder of the reaction. Pressure within the bottle reached 43 psig at 1½ hours following commencement of the reaction, and remained at that level throughout the reaction. When the reaction was complete, the bottle was unsealed and water (25 ml) was added to the reaction mixture to take up the product acid salt. Contents of the reaction vessel were then extracted with chloroform (25 ml) for removal of solvent and phenol from the aqueous phase. The resulting organic extract was in turn extracted with 25 ml of water for recovery of product, after which the aqueous phases were combined and washed with two aliquots (25 ml each) of chloroform. The aqueous phase was then stripped on a rotary evaporater to afford a gummy solid (16.1 g), and the gummy solid was dissolved in water (5 g) to provide a viscous syrup (21.1 g). This product was silylated and subjected to GLC analysis. Based on area ratios observed through GLC analysis, the product was estimated to contain about 10.6 moles 2-hydroxy-4-methylthiobutyrate per mole of 2-4-dihydroxybutyrate by-product. Use of an internal standard (n-dodecane) indicated that the product contained 50.55% 2-hydroxy-4-methylthiobutyrate. Inasmuch as the starting material (alpha-hydroxy butyrolactone) had been determined to be 92% pure, this corresponded to a yield of 77.2%.

EXAMPLE 3

Sodium hydroxide (4 g; 0.1 mole) 2,6-dimethylphenol (12.2 g; 0.1 mole) and gamma-picoline (about 75 ml) were placed in a 100 ml flask under nitrogen pressure, and reaction effected to produce sodium 2,6-dimethylphenate. The reaction product was heated to the atmospheric boiling point for removal of water. A mixture of water and gamma-picoline was distilled out of the reaction mixture overhead through a 6 inch Vigreaux columm. Temperature of the overheads ranged from 97°–145° C. during the course of the distillation.

Thereafter, the anhydrous base reagent mixture containing the sodium 2,6-dimethylphenate was transferred to a Fischer-Porter bottle. Methylmercaptan (7 g; 0.14 moles) and alpha-hydroxy butyrolactone (7.5 g; 0.073 moles) were added to the anhydrous base reagent mixture in the bottle. The bottle was then sealed and placed in an oil bath and the contents heated under autogenous pressure for a period of 5½ hours to effect conversion of the mercaptan to the sodium mercaptide and reaction of the mercaptide with the lactone to form sodium 2-hydroxy-4-methylthiobutyrate. During the course of this reaction, the temperature ranged from 105°–138° C. and the pressure from 19–37 psig. At the conclusion of the reaction, the bottle was vented and water (25 ml) was added. The diluted reaction mixture was washed with three aliquots of chloroform (25 ml each) and the combined chloroform solution was washed with an aliquot of water (25 ml). The aqueous fractions were combined and stripped on a rotary evaporator to afford a syrup which was diluted with water to a weight of 20.0 g. GLC analysis of the silylated product (n-dodecane internal standard) indicated that the sample contained 40.6% by weight 2-hydroxy-4-methythiobutyrate (HMBA) monomer and 3.5% 2,4-dihydroxybutyrate. This represented an HMBA yield of 8.1 g or 80% based on 92% purity of the starting lactone.

EXAMPLE 4

Sodium hydroxide (4 g; 0.1 mole), phenol (9.4 g; 0.1 mole), and pyridine (75 ml) were stirred under nitrogen and heated to distill pyridine/water through a 6" Vigreaux column. At the beginning of the distillation, the temperature in the pot was 112° C. and the overhead temperature was 94° C. At the conclusion of the distillation, the pot temperature was 118° C. and the overhead temperature was 114° C. About 30 to 40 g of pyridine/water were distilled off.

After water had been removed from the pot containing sodium phenate, methylmercaptan (4.8 g; 0.1 mole) was distilled, condensed in a dry ice condenser and introduced into the pot, following which addition of butyrolactone to the pot was commenced. About 15 minutes after the conclusion of the addition of methylmercaptan, all of the butyrolactone (8.6 g; 0.1 moles) had also been added. An hour and forty five minutes later, with the dry ice condenser still in place in the vent line from the pot, heat was applied to the charge mixture and reaction was thereafter continued for another 2 hr. and 10 minutes, during which time the temperature rose from 75° C. with reflux to about 105° C. The heat was then removed and, upon cooling, the reaction mixture became very thick and solids began to precipitate. By the time the mixture had cooled to room temperature, the batch was essentially solid.

At this point, water (20 g) was added and the resulting mixture heated to 98° C. and allowed to cool. A homogeneous solution was obtained which was then washed in three aliquots of chloroform (25 ml each). The raffinate was stripped on a rotary evaporator and stored in a vacuum oven at 100° C. where it dried to a solid (13.7 g). GLC analysis of the silylated product indicated 34.2 area % $HOCH_2CH_2CH_2CO_2Na$, 63.9 area % $CH_3SCH_2CH_2CH_2CO_2Na$ and 1.7 area % unknown higher boiling materials.

EXAMPLE 5

Sodium hydroxide pellets (4 g; 0.1 mole), phenol (9.4 g; 0.1 mole), and pyridine (75 ml) were placed in a 100 ml three neck round bottom flask and heated to distill pyridine/$H_2O$ through a 6" Vigreaux column. About 30 to 40 ml pyridine/$H_2O$ distilled over, with a final overhead temperature of 113° C.

On the next day methylmercaptan was distilled, condensed in a dry ice condenser, and introduced into the bottom fraction remaining in the pot from the pyridine/water distillation. After all of the methylmercaptan (about 5 g) had been added, and with the dry ice condenser in operation on the vent line from the pot, heat was applied to the pot and butyrolactone (8.6 g) was added while the methylmercaptan was refluxing at atmospheric pressure. After the lactone had all been added, heating continued under reflux. About one half hour after the completion of the addition of lactone, the reaction mass had reached a temperature of 99° C. and, at this point, the heat was turned off.

After the mass had cooled to a temperature of about 48° C., water (20 g) was added and heat reapplied. When the temperature reached about 63° C., all the solids had dissolved. At this point, additional water (5 g) was added to the solution and heating was continued for another ten minutes, raising the temperature to 86° C. The heat was then withdrawn and the solution allowed to cool for about 1 hour and 45 minutes. The cooled solution was washed with three aliquots of chloroform (25 ml each), then reduced on a rotary evaporator. The residue was dried by storing it in a vacuum oven at 100° C. The dried solid weighed 13.7 g. Analysis of the silylated product by GLC showed 44.5 area % $HOCH_2CH_2CH_2CO_2Na$, 54.3% $CH_3SCH_2CH_2CH_2CO_2Na$, and 1.0% of an unknown high boiler.

EXAMPLE 6

Sodium hydroxide (4 g; 0.1 mole), phenol (9.4 g; 0.1 mole), and pyridine (75 ml) were placed in a 100 ml capacity three neck round bottom flask under $N_2$. Heat was applied and a fraction (about 30 ml) of pyridine/$H_2O$ was distilled off through a 6" Vigreaux column (overhead temperature=98°–114° C.).

Methylmercaptan (5 g) was distilled, condensed in a dry ice condenser, and introduced into the resulting solution of sodium phenate in pyridine. Introduction of methylmercaptan was carried out slowly over a period of about one and one half hours.

With the dry ice condenser in operation on the vent line from the flask, heat was applied to the mixture in the flask. Within about ten minutes, the mixture reached a temperature of about 75° C. under reflux. At this point, addition of butyrolactone to the mixture was commenced. A total of 8.6 g of butyrolactone was added over a period of about ten minutes. By the time the addition was completed, the temperature of the mixture had risen to 78° C. Heating was continued for another 2 hours and 15 minutes, during which time the temperature rose to 114° C. Heat was then removed and the mixture allowed to cool.

On the next day, water (25 ml) was added to the cooled mixture and heat thereupon applied. Within about 35 minutes, the temperature had risen to 96° C. and the mixture had become a homogeneous solution. Heat was then removed. After the mixture had cooled, it was washed three times with 25 ml aliquots of chloroform for extraction of phenol, pyridine and organic impurities. The aqueous raffinate was then stripped on a rotary evaporator, and the residue dried by storage under vacuum at a temperature of 100°–110° C. The dry solid product (14.1 g) was silylated and analyzed by GLC, and found to contain 28.8% $HOCH_2CH_2CH_2CO_2Na$, 67.3% $CH_3SCH_2CH_2CH_2CO_2Na$, and 3.4% unknown.

EXAMPLE 7

Sodium hydroxide (4 g; 0.1 mole) and phenol (9.4 g; 0.1 mole) were dissolved in pyridine (75 ml). Heat was applied to the resulting mixture and a water/pyridine fraction (25 ml) was distilled overhead through a 6" Vigreaux column. The temperature of the overheads ranged from 96°–113° C. during the course of the distillation.

Into the resulting dry solution of sodium phenate in pyridine, methylmercaptan (5.5 g) was introduced by distilling it slowly from another source, condensing the vapor in a dry ice condenser, and allowing the condensate to flow by gravity into the phenate solution. Introduction of methylmercaptan took place over a period of about one hour and 40 minutes. After addition of the methylmercaptan was complete, and with the dry ice condenser in place on the vent line from the vessel containing the resulting mixture, heat was applied to the mixture and addition of butyrolactone was commenced. Over a period of about 5 minutes a total of 4.3 g of butyrolactone was added. When this addition had been completed, the temperature of the mixture was about 75° C. Heating was continued and, when the temperature reached 77° C., the solids in the mixture had completely dissolved. Heating was carried out for another hour, during which time the temperature rose to about 86° C.

Later sodium bicarbonate (5 g) and water (25 ml) were added to the reaction mass and heat was applied. Within about one half hour, the temperature rose to about 96° C., at which point the heat was removed. The aqueous mixture was then allowed to cool, after which it was washed three times with 25 ml aliquots of chloroform. The aqueous raffinate was then stripped on a rotary evaporator to afford a solid residue (13.1 g). This product was silylated and analyzed by GLC and found to contain the following relative levels (area %) of volatile components: 18.2% $HOCH_2CH_2CH_2CO_2Na$, 80.3% $CH_3SCH_2CH_2CH_2CO_2Na$, and 0.4% unknown peak.

EXAMPLE 8

Sodium hydroxide (4 g) and phenol (9.4) were dissolved in pyridine (75 ml) and about 25 ml of a pyridine/water fraction distilled over through a Vigreaux column. The overhead temperature ranged from 94°–114° C. during the distillation.

The solution of sodium phenate in pyridine was placed in a Fisher-Porter bottle and cooled in an ice bath. Then methylmercaptan (10 g) and gamma-butyrolactone (8.6 g) were introduced into the solution in the bottle. The bottle was sealed and stirred with a magnetic stirrer. Heat was then applied and reaction carried out under autogenous pressure for a period of about 2 hours and 55 minutes. During this time the temperature rose to 89° C. and the pressure in the bottle reached a maximum of about 21 psig. Heat was then removed. After the contents of the bottle had cooled to about room temperature, it was vented to the atmosphere and water (25 ml) was added to the mixture. The resulting aqueous mixture was washed with chloroform (three aliquots of 25 ml each), and the aqueous raffinate was then stripped on a rotary evaporator, yielding a residue weighing about 14.9 g.

GLC analysis of the silylated product indicated the following area % of volatile constituents: 21.6% $HOCH_2CH_2CH_2CO_2Na$, 77.4% $CH_3SCH_2CH_2CH_2CO_2Na$, and an unknown high boiler peak of 0.4%.

EXAMPLE 9

Sodium hydroxide (4 g) and phenol (9.4 g) were dissolved in gamma-picoline (about 75 ml). Heat was applied to the resulting mixture to effect formation of sodium phenate and to distill off a fraction comprising water and picoline (about 25 ml). The overhead temperature ranged from 96°–144° C. during the distillation.

The resulting solution of sodium phenate in picoline was placed in a Fisher-Porter bottle, to which methylmercaptan (10.3 g) and butyrolactone (8.6 g) were also added. The bottle was then sealed and placed in a water bath and heat was applied to the contents thereof to effect reaction under autogenous pressure. Heating was continued over a period of about 2 hours and 15 minutes, during which time the temperature rose to about 95° C. and the pressure reached a maximum of about 22 psig. One half hour after the heat was removed, the bottle was vented to the atmosphere, and water (25 ml) added to the mixture contained in the bottle.

The resulting aqueous mixture was washed three times with aliquots of chloroform (25 ml each), and the aqueous raffinate thereafter stripped on a rotary evaporator, yielding 13.9 g of solid product. GLC analysis of the silylated product indicated the following composition (area %) of the volatile components: 0.8% phenol; 19.1% $HOCH_2CH_2CH_2CO_2Na$, 79.1% $CH_3SCH_2CH_2CH_2CO_2Na$, and 0.5% of high boilers.

EXAMPLE 10

Sodium hydroxide (4g) and phenol (9.4 g) were dissolved in gamma-picoline (about 75 ml). Heat was applied to effect formation of sodium phenate and to remove water from the system. Approximately 25 ml of a water/picoline fraction was distilled overhead through a 6″ Vigreaux column. Temperature of the overheads during the reaction and distillation ranged from 96°–144° C.

The resulting solution of sodium phenate in picoline was placed in a Fisher-Porter bottle. Also added to the bottle were methylmercaptan (10 g) and butyrolactone (8.6 g). The bottle was sealed and placed on an oil bath. Heat was applied via the oil bath. Reaction ensued under autogenous pressure. During the reaction the temperature rose to 120° C., and the pressure reached a maximum of 36 psig. After about 2 hours and 15 minutes, heat was removed. When the reaction mass had cooled for about one half hour, water (25 ml) was added thereto.

The resultant aqueous mixture was then washed three times with 25 ml aliquots of chloroform. The aqueous raffinate was stripped on a rotary evaporator, affording a solid residue (15.3 g), a sample of which was silylated and subjected to GLC analysis. The results showed the following composition of volatile products: 0.3% phenol, 13.5% $HOCH_2CH_2CH_2CO_2Na$, 84.9% $CH_3SCH_2CH_2CH_2CO_2Na$, and 0.97% of a high boiler peak.

EXAMPLE 11

Sodium hydroxide (4 g) and 2,6-dimethylphenol (12.2 g) were dissolved in gamma-picoline (about 75 ml). Heat was applied to the mixture to remove water from the mixture. About 25 ml of a water/picoline mixture were distilled overhead through a 6″ Vigreaux column. The temperature of the overheads during the reaction and distillation ranged from 110°–144° C.

The resulting solution of sodium 2,6-dimethylphenate in picoline was placed in a Fisher Porter bottle, along with methylmercaptan (about 10.4 g) and butyrolactone (8.5 g). The bottle was then sealed and placed in an oil bath. Heat was applied via the oil bath and reaction carried out under autogenous pressure. Heating was maintained over a period of about 2 and ½ hours, during which time the temperature rose to 131° C. and the pressure reached a maxiumum of about 28 psig. About 15 minutes after the heat had been removed, the bottle was vented to the atmosphere and water (25 ml) added to the reaction mass.

The resulting aqueous mixture was washed three times with 25 ml aliquots of chloroform, and the remaining aqueous phase was stripped on a rotary evaporator to afford 14.2 g of solid product. GLC analysis of this product (silylated) indicated the following relative composition of volatile components: 11.0% $HOCH_2CH_2CH_2CO_2Na$, 88.1% $CH_3SCH_2CH_2CH_2CO_2Na$. There was no appreciable peak which could be attributed to high boilers.

What is claimed is:

1. A process for the preparation of a compound corresponding to the formula:

$$R^1-S-(CH_2)_n-CH(R^2)-C(O)-OM$$

where $R^1$ comprises a lower alkyl group, M is alkali metal, n is an integer between 2 and 4, inclusive and $R^2$ is selected from the group consisting of hydrogen, hydroxyl, amino, $-OR^3$, and $-NH-R^4$ where $R^3$ is selected from the group consisting of alkyl and aryl, and $R^4$ is selected from the group consisting of alkyl, aryl, and acyl, the process comprising:

reacting a lower alkyl mercaptan corresponding to the formula:

R¹—SH, where R¹ is as defined above, with an alkali metal phenate to produce an alkali metal mercaptide corresponding to the formula:

R¹—S—M where R¹ and M are as defined above; and reacting said alkali metal mercaptide, in the presence of an aprotic polar organic solvent, with a lactone corresponding to the formula

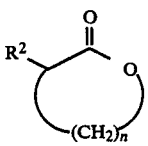

where R² and n are as defined above.

2. A process as set forth in claim 1 wherein said solvent has a dipole moment greater than 1 and a dielectric constant of greater than about 10.

3. A process as set forth in claim 2 wherein said solvent is selected from the group consisting of dimethylformamide, hexamethylphosphoric triamide, dimethyl sulfoxide, tetramethylurea, pyridine, and ring substituted alkyl pyridines.

4. A process as set forth in claim 3 wherein said solvent comprises pyridine or a ring substituted alkyl pyridine.

5. A process as set forth in claim 1 wherein said alkali metal mercaptide is reacted with said lactone at a temperature of between about 80° and about 150° C.

6. A process as set forth in claim 1 wherein between about 1 and about 3 moles of said alkali metal mercaptide are charged per mole of said lactone.

7. A process as set forth in claim 1 wherein R¹ is methyl and R² is hydroxyl.

8. A process for the preparation of an alkythioalkanoate compound corresponding to the formula

R¹—S—(CH₂)ₙ—CH(R²)—C(O)—OM where R¹ comprises a lower alkyl group, M is alkali metal, n is an integer between 2 and 4, inclusive, and R² is selected from the group consisting of hydrogen, hydroxyl, amino,

—OR³ and

—NH—R⁴ where R³ is selected from the group consisting of alkyl and aryl, and R⁴ is selected from the group consisting of alkyl, aryl, and acyl, the process comprising admixing and reacting, in the presence of an aprotic polar organic solvent, a lower alkyl mercaptan corresponding to the formula:

R¹—S—H where R¹ is as defined above, an alkali metal phenate, and a lactone corresponding to the formula:

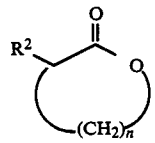

where R² is as defined above; and maintaining the resulting mixture at a temperature of at least 80° C. for a time sufficient to form said alkylthioalkanoate compound.

9. A process as set forth in claim 8 wherein said solvent has a dipole moment greater than 1 and a dielectric constant greater than about 10.

10. A process as set forth in claim 9 wherein said solvent is selected from the group consisting of dimethylformamide, hexamethylphosphoric triamide, dimethyl sulfoxide, tetramethylurea, pyridine, and ring substituted alkyl pyridines.

11. A process as set forth in claim 10 wherein said solvent is selected from the group consisting of pyridine and ring substituted alkyl pyridines.

12. A process as set forth in claim 8 wherein the reaction is carried out in a system to which said lower alkyl mercaptan and said lactone are charged in a ratio of between about 1 and about 3 moles of said lower alkyl mercaptan per mole of said lactone.

13. A process as set forth in claim 8 wherein R¹ is methyl and R² is hydroxyl.

14. A process for the preparation of a compound corresponding to the formula:

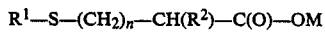
R¹—S—(CH₂)ₙ—CH(R²)—C(O)—OM where R¹ comprises a lower alkyl group, M is alkali metal, n is an integer between 2 and 4 inclusive, and R² is selected from the group consisting of hydrogen, hydroxyl, amino,

—OR³ and

—NH—R⁴ where R³ is selected from the group consisting of alkyl and aryl, and R⁴ is selected from the group consisting of alkyl, aryl, and acyl, the process comprising the steps of:

reacting a substituted or unsubstituted phenol with an alkali metal hydroxide in a crude base reaction system comprising a solvent selected from the group consisting of pyridine and aprotic ring substituted pyridines that form low boiling azeotropes with water;

removing water from said crude base reaction system by azeotropic distillation, thereby forming a substantially anhydrous base reagent mixture containing an alkali metal phenate;

reacting a lower alkyl mercaptan corresponding to the formula:

R¹—S—H where R¹ is defined above, with said alkali metal phenate, thereby producing an alkali metal mercaptide corresponding to the formula:

R¹—S—M where $R^1$ and M are as defined above; and reacting said alkali metal mercaptide, in the presence of an aprotic polar organic solvent, with a lactone corresponding to the formula:

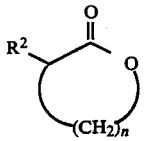

where $R^2$ and n are as defined above.

15. A process as set forth in claim 14 wherein said alkali metal mercaptide is formed by reacting said alkylmercaptan with said alkali metal phenate in said anhydrous base reagent system.

16. A process as set forth in claim 15 wherein said lactone is reacted with said alkali metal mercaptide in the presence of a solvent selected from a group consisting of pyridine and ring substituted alkyl pyridines.

17. A process as set forth in claim 16 wherein said process is carried out in a system to which said mercaptan and said lactone are charged in a ratio of between about 1 and about 3 moles of said mercaptan per mole of said lactone.

18. A process as set forth in claim 14 wherein $R^1$ is methyl and $R^2$ is hydroxyl.

19. A process for the preparation of an alkylthioalkanoate compound corresponding to the formula:

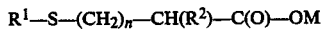

where $R^1$ comprises a lower alkyl group, M is alkali metal, n is an integer between 2 and 4, inclusive, and $R^2$ is selected from the group consisting of hydrogen, hydroxyl, amino, —$OR^3$ and

—NH—$R^4$ where $R^3$ is selected from the group consisting of alkyl and aryl, and $R^4$ is selected, from the group consisting of alkyl, aryl, and acyl, the process comprising the steps of:

reacting a substituted or unsubstituted phenol with an alkali metal hydroxide in a crude base reaction system comprising a solvent selected from the group consisting of pyridine and aprotic ring substituted pyridines that form low boiling azeotropes with water;

removing water from said crude base reaction system by azeotropic distillation, thereby forming a substantially anhydrous base reagent mixture;

preparing a final reaction mixture by admixing with said anhydrous base reagent mixture a lower alkylmercaptan corresponding to the formula:

where $R^1$ is as defined above, and a lactone corresponding to the formula:

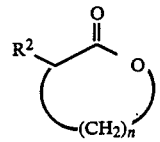

where $R^2$ and n are as defined above; and maintaining the final reaction mixture at a temperature of at least 80° C. for a time sufficient to form said alkylthioalkanoate compound.

20. A process as set forth in claim 19 wherein said solvent has a dipole moment of at least 1 and a dielectric constant of least about 10.

21. A process as set forth in claim 20 wherein said solvent is selected from the group consisting of dimethylformamide, hexamethylphosphoric triamide, dimethyl sulfoxide, tetramethylurea, pyridine, and ring substituted alkyl pyridines.

22. A process as set forth in claim 21 wherein said solvent comprises pyridine or a ring substituted alkyl pyridine.

23. A process for the preparation of a compound corresponding to the formula:

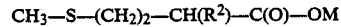

where M is alkali metal and $R^2$ is selected from the group consisting of hydrogen, hydroxyl, amino, —$OR^3$ and

—N—$R^4$ where $R^3$ is selected from the group consisting of alkyl and aryl, and $R^4$ is selected from the group consisting of alkyl, aryl, and acyl, the process comprising reacting methylmercaptan with an alkali metal phenate to produce a alkali metal methylmercaptide corresponding to the forumla:

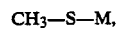

where M is as defined above; and reacting said alkali metal methylmercaptide, in the presence of an aprotic polar organic solvent, with a lactone corresponding to the formula:

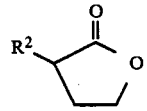

where $R^2$ is as defined above.

24. A process for the preparation of a methylthiobutyrate compound corresponding to the formula:

where M is alkali metal and $R^2$ is selected from the group consisting of hydrogen, hydroxyl, amino, —$OR^3$ and

—NH—$R^4$ where $R^3$ is selected from the group consisting of alkyl and aryl, and $R^4$ is selected from the group consisting of alkyl, aryl, and acyl, the process comprising admixing and reacting, in the presence of an aprotic polar organic solvent, methylmercaptan, an alkali metal phenate and a lactone corresponding to the formula:

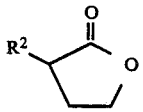

where $R^2$ is as defined above; and
maintaining the resulting mixture at a temperature of at least 80° C. for a time sufficient to form said methylthiobutyrate compound.

25. A process for the preparation of a compound corresponding to the formula:

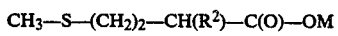

where M is alkali metal and $R^2$ is selected from the group consisting of hydrogen, hydroxyl, amino, —$OR_3$ and

—NH—$R^4$ where $R^3$ is selected from the group consisting of alkyl and aryl, and $R^4$ is selected from the group consisting of alkyl, aryl, and acyl, the process comprising the steps of:
reacting a substituted or unsubstituted phenol with an alkali metal hydroxide in a crude base reaction system comprising a solvent selected from the group consisting of pyridine and aprotic ring substituted pyridines that form low boiling azeotropes with water;
removing water from said crude base reaction system by azeotropic distillation, thereby forming a substantially anhydrous base reagent mixture containing an alkali metal phenate;
reacting methylmercaptan with said alkali metal phenate, thereby producing an alkali metal mercaptide corresponding to the formula:

where M is as defined above; and reacting said alkali metal mercaptide, in the presence of an aprotic polar organic solvent, with a lactone corresponding to the formula:

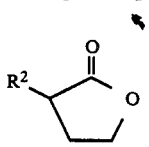

where $R^2$ is as defined above.

26. A process for the preparation of a methylthiobutyrate compound corresponding to the formula:

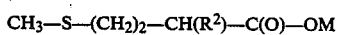

where M is alkali metal and $R^2$ is selected from the group consisting of hydrogen, hydroxyl, amino, —$OR^3$ and

—NH—$R^4$ where $R^3$ is selected from the group consisting of alkyl and aryl, and $R^4$ is selected from the group consisting of alky, aryl, and acyl, the process comprising the steps of:
reacting a substituted or unsubstituted phenol with an alkali metal hydroxide in a crude base reaction system comprising a solvent selected from the group consisting of pyridine and aprotic ring substituted pyridines that form low boiling azeotropes with water;
removing water from said crude base reaction system by azeotropic distillation, thereby forming a substantially anhydrous base reagent mixture;
preparing a final reaction mixture by admixing with said anhydrous base reagent mixture methylmercaptan and a lactone corresponding to the formula:

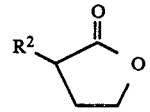

where $R^2$ is as defined above; and
maintaining the final reaction mixture at a temperature of at least about 80° C. for a time sufficient to form said methylthiobutyrate compound.

* * * * *